United States Patent [19]
Atwood et al.

[11] 3,948,607
[45] Apr. 6, 1976

[54] TRANSFER SYSTEM FOR USE IN ANALYSIS APPARATUS

[75] Inventors: John G. Atwood, Redding; Lucien C. Ducret, Riverside; Hamilton W. Marshall, Jr., Ridgefield, all of Conn.

[73] Assignee: The Perkin-Elmer Corporation, Norwalk, Conn.

[22] Filed: Aug. 22, 1974

[21] Appl. No.: 499,618

[52] U.S. Cl.................. 23/259; 23/253 R; 137/154
[51] Int. Cl.²... F04F 1/00; G01N 1/14; G01N 1/18; G01N 21/26
[58] Field of Search.. 23/259, 253 R, 230 A, 253 A; 73/423 R, 423 A; 137/154

[56] References Cited
UNITED STATES PATENTS

| | | |
|---|---|---|
| 3,197,285 | 7/1965 | Rosen ............................ 23/259 X |
| 3,427,135 | 2/1969 | Pelavin et al. .................... 23/253 R |
| 3,475,130 | 10/1969 | Baruch ............................ 23/253 R |
| 3,524,366 | 8/1970 | Hrdina ............................ 137/154 X |
| 3,594,129 | 7/1971 | Jones .............................. 23/259 X |
| 3,800,984 | 4/1974 | Phelan ............................ 23/259 |

Primary Examiner—Robert M. Reese
Attorney, Agent, or Firm—S. A. Giarratana; F. L. Masselle; J. K. Conant

[57] ABSTRACT

An automatic transfer system for transferring a reaction sample to a sample cell in analysis apparatus in which a transfer pump draws in slugs of sample separated by slugs of air, the slugs being obtained through a coordinated probe oscillation, bringing a sample slug into the sample cell and holding it there for measurement, the system further including a wash pump for the depositing wash liquid in the sample cup which is also drawn into the system to flush it out between samples.

9 Claims, 2 Drawing Figures 3,948,607

TRANSFER SYSTEM FOR USE IN ANALYSIS APPARATUS

BACKGROUND OF THE INVENTION

This invention relates to analysis apparatus in general and more particularly to an improved automatic transfer system for use in kinetic analysis apparatus or the like.

In an application of John G. Atwood et al Ser. No. 499,602 filed on Aug. 22, 1974 and assigned to the same assignee as the present invention, completely automated apparatus is disclosed for kinetic analysis of human serum for determination of enzymes therein. One of the basic needs of an apparatus of that nature and other similar apparatus is a transfer system for conveying reaction mixture samples or batches to a photometer sample cell where absorbance can be measured. Such an apparatus must transfer the sample reliably and accurately so that the cell is properly filled. Furthermore, it must include means to endure that sample carryover is minimized and in a system of the disclosed nature which operates using micro quantities, all this must be done with extremely small amounts of liquids.

SUMMARY OF THE INVENTION

The present invention provides a transfer system which fills the above noted needs. Transfer of the sample or batch of a fluid reaction mixture to the photometer cell is accomplished by a transfer system which has very low carryover from sample to sample yet works extremely rapidly with very small sample volumes. This is achieved through the combination of a cam-driven positive displacement transfer pump; a cam-driven transfer probe, which dips into a reaction cup containing the sample, oscillating up and down in a controlled way to produce air slugs in between sample slugs; a cam-driven wash liquid pump that discharges a measured amount of wash liquid into the cup after the sample is exhausted; and a valve which stops the sample flow through the photometric cell during measurement. The wash liquid chemically conditions the system between reactant samples and washes out carryover. The cam-driven sample pump momentarily reverses the flow once each transfer cycle to dislodge any foreign matter that may have deposited in the probe or cell. All the cams (i.e., the cams for the transfer pump, probe motion, wash liquid pump and valve motion) are coordinated on a single shaft to make the complex interrelated motion occur in a closely timed pattern.

DETAILED DESCRIPTION OF THE PREFERRED EMBODIMENT

Figure 1:
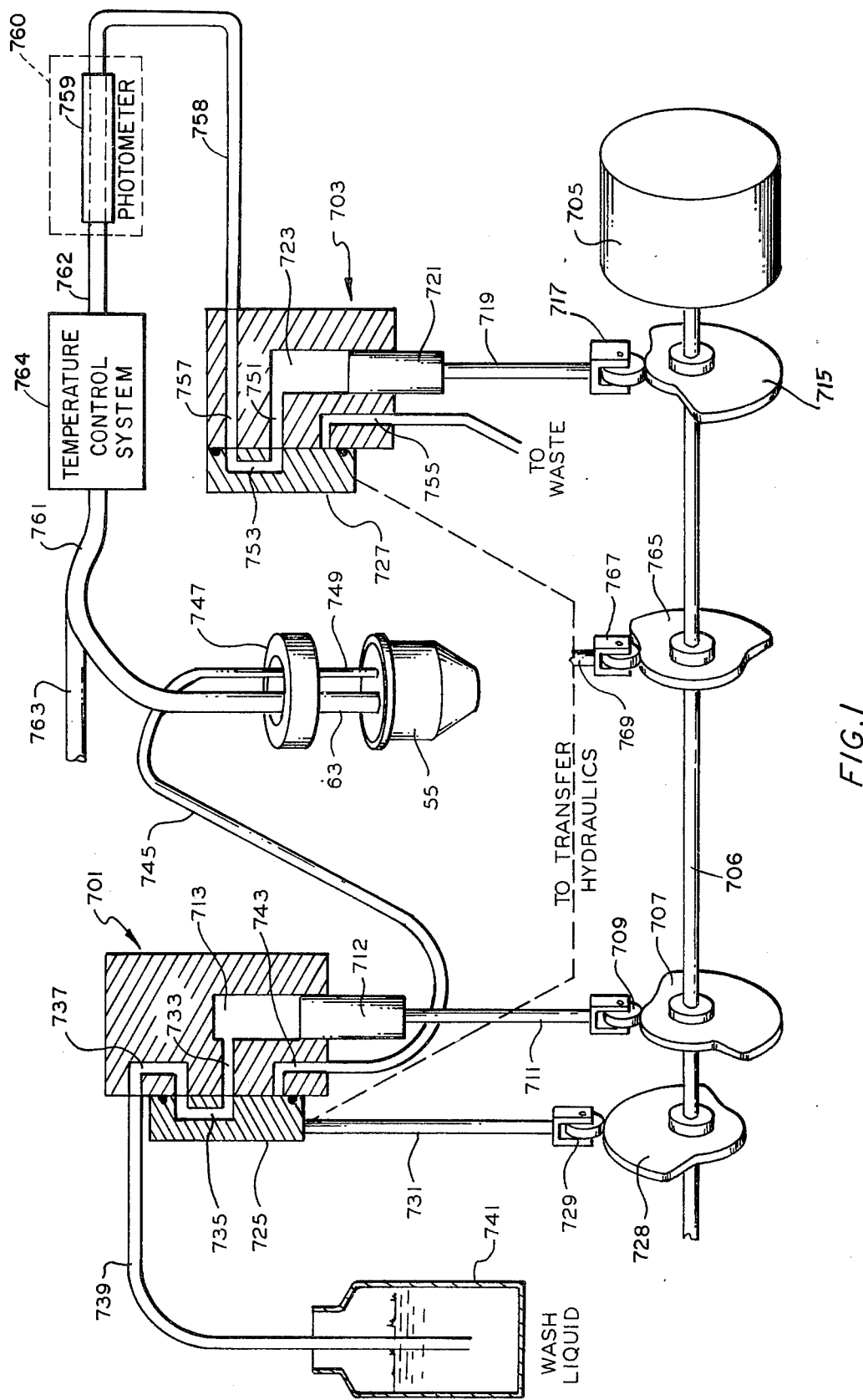
FIG. 1 is a schematic illustration of the transfer pump of the present invention.

FIG. 1 illustrates the construction of the transfer pump of the present invention for transferring a fluid reaction mixture sample consisting of human serum and two reagents to a photometer sample cell. Once a serum specimen has been mixed with the two reagents, stirred, and allowed to incubate for the required period of time, the transfer mechanism must pick up the proper amount of the sample, transfer it to the photometer cell where it is analyzed and then wash out the transfer system in preparation for the next sample or batch of reaction mixture. Thus, on FIG. 1, there are shown two pumps, one of which is a wash pump indicated generally as 701 and the other of which is the transfer pump designated 703. These pumps are driven by a motor 705 having cams on its shaft 706. Pump 701 is driven by a cam 707 coupled through a cam follower 709 and pushrod 711 operating a piston 712 within a cylinder 713. The pump 703 is driven by a cam 715 engaged by a cam follower 717 on the end of a pushrod 719 which operates a piston 721 within a cylinder bore 723.

A slide valve member 723 associated with pump 701 and a slide valve member 727 associated with pump 703 are jointly driven by a single cam 728 operating through a cam follower 729 and pushrod 731. Cylinder 713 has a single inlet-outlet port and passage 733 which, depending on the position of valve member 725, can be coupled via passage 735 in the valve member either to a passage 737, from which a conduit 739 extends into a wash liquid container 741, or to a passage 743 coupled by a conduit 745 to a sponge-holding wiper unit 747 through which a reaction mixture transfer probe 63 extends. A tube 749 extending from the conduit 745 is formed into wiper unit 747 and terminates at a position above a reaction cup 55.

Transfer pump 703 has a single inlet-outlet port and passage 751 which, depending on the position of valve member 727, can be coupled via valve member passage 753 either to an outlet passage 755 leading to a waste receptacle or to a passage 757 which is coupled via a conduit 758 to one (the outlet) end of the photometer cell 759 of a photometer system 760. The other (inlet) end of cell 759 is connected via conduit 762 to the outlet of a temperature control system 764 which has its inlet connected via a flexible tube 761 to a transfer probe 63 which is positioned over a reaction cup 55 by a support arm 763 as will be described presently. Temperature control system 762 is designed to regulate the temperature of reaction mixture passing from probe 63 to photometer cell 759 in a manner described and illustrated in detail in the aforementioned copending application Serial No. 499,602.

At the beginning of the cycle, the valve 727 is at its uppermost position (as shown in FIG. 1) coupling port 751 with passage 757 and piston 721 is near the top of its stroke in cylinder 723. At this point, the previous sample is within the cell 759 and a quantity of wash liquid in the probe 63 and tubing 761. The manner in which this occurs will become evident from the following description. The cam 715 is constructed so that it first causes piston 721 to move upward slightly displacing the liquid within the passage 757, conduit 758, cell 759, tubing 761 and probe 63 a slight distance toward the cup 55. The purpose of this slight movement is to dislodge any solid material which may be lodged in the system. Piston 721 then begins its downward stroke creating suction at probe 63; simultaneously the probe itself is caused to oscillate up and down by apparatus to be described presently in connection with FIG. 2. (This apparatus is driven by motor 705 through a cam 765, cam follower 767, and pushrod 769 which appear in FIG. 1). Probe 63 dips into the sample eight times, picking up a small volume of sample each time. Each oscillation carries the probe a little farther down as the sample level falls and finally, the probe goes all the way to the bottom and stays there for a longer period of time so as to draw a sufficient quantity of sample to fill photometer cell 759. The result is eight small slugs of sample separated by air bubbles followed by a large sample slug for analysis. The large slug of the sample is approximately 25 microliters and more than fills the 18 to 19 microliter capacity of the photometer cell 759. At this time, the valve member 725 is in a position to couple port 733 to outlet passage 743 and piston 712 is driven upward in the cylinder 713 which was previously filled with wash liquid. The wash liquid is thus forced out through the conduit 745 and tube 749 into the cup 55. Transfer probe 63 continues to oscillate and the piston 721 continues to retract drawings slugs of wash liquid separated by air bubbles into the probe 63 and tube 761. When the piston 721 reaches the bottom of its travel, the new sample will be in the photometer cell 759 which will have been washed out previously by the wash liquid which was within the probe 63 and tube 761 at the beginning of the cycle. Portions of previous wash liquid and samples will be within the cylinder 723. At this stage, the sample is properly positioned in the photometer cell and, valve 727 is moved to its lowermost position, sealing off passage 757 so that the sample cannot move and analysis then takes place. During analysis piston 721 is moved upwardly in cylinder 723 discharging the waste through the port 751, passage 753 in valve member 727 and out through the passage 755 to waste. At the same time valve member 725 is in the position shown in FIG. 1 and, piston 712 of the wash pump 701 is caused to move downward to draw in new wash liquid through the tube 739, passage 737, valve member passage 735, and port 733 to the cylinder 713. The transfer pump is now ready for another cycle.

Figure 2:
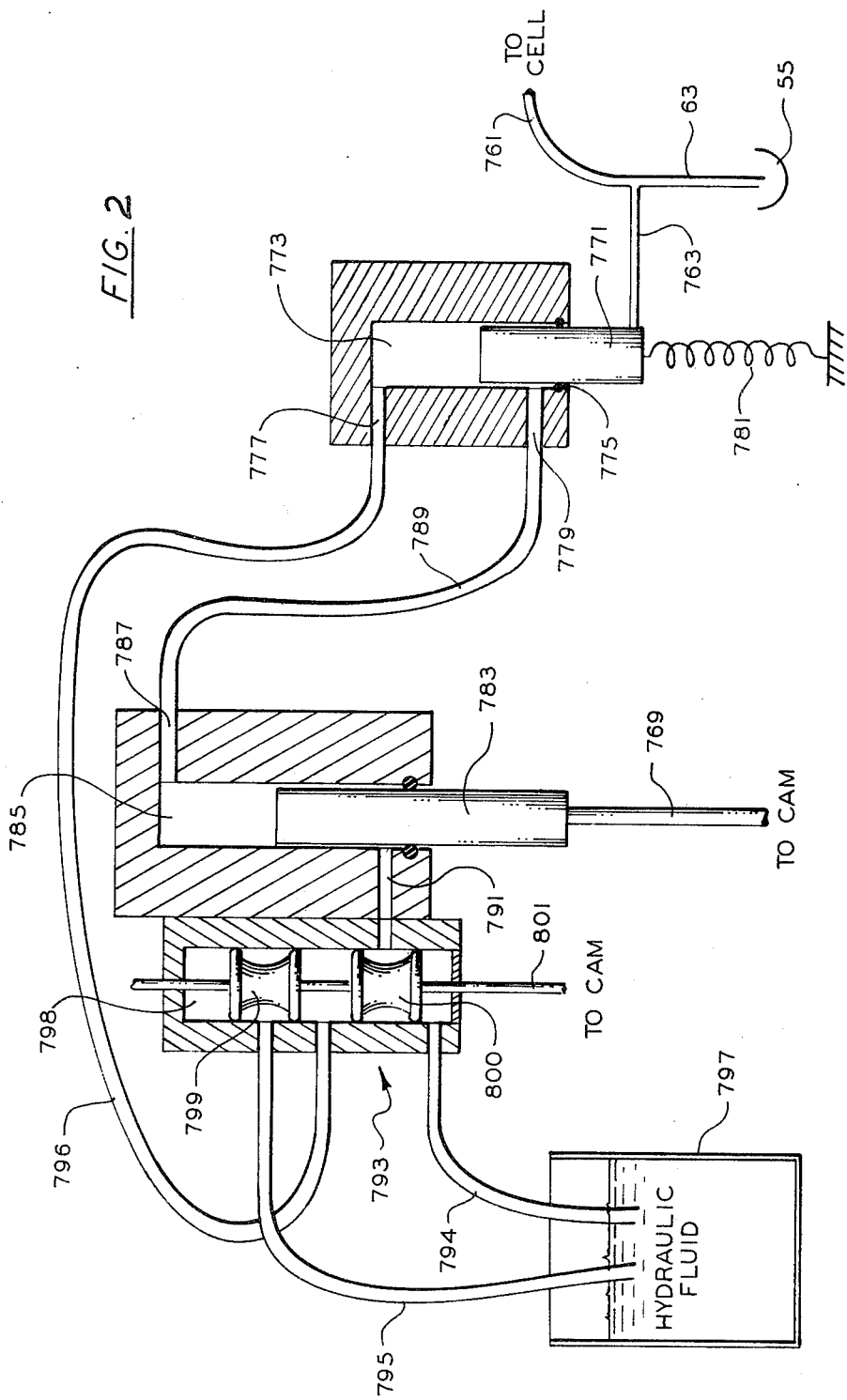
FIG. 2 is a similar illustration of the hydraulic portion of the transfer system which provides oscillating probe motion.

FIG. 2 illustrates the manner in which transfer probe oscillation is obtained. The probe arm 763 is mounted to a hydraulic piston 771 operating in a cylinder 773. An appropriate seal 755 is provided at the bottom of the cylinder in conventional fashion. The cylinder 773 has two ports designated 777 and 779. Piston 771 is spring loaded with a spring 781 which tends to push the piston upwardly withdrawing the probe 63 from the cup 55. Piston 771 is a slave piston driven by the displacement of a piston 783 operating in a master cylinder 785 having a port 787 is connected with appropriate tubing 789 to the port 779. Cylinder 785 has a second port 791 which connects with a spindle valve 793. Other connections to the spindle valve 793 are two hydraulic lines 794 and 795 having free ends immersed in a hydraulic fluid container 797 and a line 796 coupled to the port 777 of cylinder 773. The piston 783 is coupled through pushrod 769 to a cam follower 767 engaging cam 765 as shown on FIG. 1. The spindle valve comprises a bore 798 with two spindles 799 and 800 operating therein on a rod 801 coupled to the valve cam 727 of FIG. 1.

At the portion of the cycle where the probe 63 must oscillate up and down in the sample, the valve 793 is in the position shown. In this position, the port 791 is closed off as is the connection through tube 796 with the port 777 of the cylinder 773. The cam causes the master piston 783 to oscillate up and down with each movement bringing it closer to the top; Pressure in slave cylinder 773 fluctuates accordingly in well known fashion causing piston 771 to follow the motion of the master piston. Preferably, the diameter of the master cylinder 785 is much larger than that of the slave cylinder 773 so that a multiplication of stroke length will take place. In other words, a small ocillatory displacement at the cylinder 785 will cause a large oscillating motion at the probe 63. When all of the liquid (both sample and wash liquid) has been drawn into the probe, the valve stem 801 is moved upward by cam 765 coupling port 791 with hydraulic line 794 and coupling lines 795 and 796, thus permitting the pressure of spring 781 to push piston 771 upward, forcing hydraulic fluid from cylinder 773 through ports 777, valve tube 796, bore 798 and line 795 to the hydraulic fluid reservoir 796. During this upward travel of piston 771, fluid can flow through another path, i.e., through port 779 and tube 789 to cylinder 785. However, the resistance to flow through this second path is much greater and the path of least resistance available through the port 777 will be taken. Thus, the piston 771 will move fully upward under the force of spring 781 expelling essentially all the hydraulic fluid contained in cylinder 773. At this time, the piston 783 is essentially at the top of its stroke and starts to move downward to draw in a new supply of hydraulic fluid through the line 794, the segment of valve bore 798 below spindle 800, and port 791 to the cylinder 785. Again, an other path through the spindle 799 and through the cylinder 773 exists. But thus path will have the greater resistance so that the fluid will be drawn in through the line 794. This operation results in a circulating of the hydraulic fluid on each cycle and causes any air entrapped in the system to be eliminated. It also gives the system a self-priming operation, so that after being shut down to the extent where the hydraulic fluid has drained out of the cylinders, it will still be able to start up quickly without priming.

Thus, an improved transfer system for use in automatic analysis apparatus has been shown. Although specified embodiments have been illustrated and described it will be obvious to those skilled in the art that various modifications may be made without departing from the spirit of the invention which is intended to be limited solely by the appended claims.

What is claimed is:

1. A method of transferring a reaction mixture sample to a photometer sample cell comprising:

a. positioning a transfer probe above a reaction cup containing said mixture sample, said probe being flow-coupled in series with the sample of a photometer system;

b. applying suction to said photometer cell to create a partial vacuum in said probe using positive displacement means;

c. oscillating said probe up and down whereby said probe will alternately draw in slugs of air and slugs of said reaction mixture sample;

d. continuing to apply suction to said photometer cell until one slug of said reaction mixture sample is located in and completely fills said photometer cell;

e. immobilizing said one slug in said photometer cell while photometrically analyzing same;

f. discharging a wash liquid into said cup after said reaction mixture sample has been withdrawn therefrom;

g. after completion of step e, appling suction to said photometer cell while continuing oscillation of said probe to draw into said probe and through said photometer cell a plurality of slugs of wash liquid separated by slugs of air; and h. discharging the wash liquid to waste.

2. A method according to claim 1 further including the step of bringing said reaction mixture sample to a predetermined temperature during transfer.

3. A method according to claim 1 further including the step of applying a pressure to said photometer cell momentarily prior to applying suction, to dislodge any material within the photometer cell or probe.

4. Apparatus to transfer a reaction mixture sample from a reaction cup to a photometer sample cell comprising:
   a. a transfer probe;
   b. conduit means flow-coupling said probe to the sample cell;
   c. means defining a conduit from said sample cell to an outlet;
   d. controlled positive displacement means to apply suction to the outlet and thereby create a partial vacuum in said cell and said probe;
   e. means to oscillate said probe up and down, into and out of the cup to draw in through said probe and cell a plurality of slugs of reaction mixture sample separated by air slugs;
   f. means for temporarily immobilizing a slug of sample occupying and filling said cell; and
   g. means to discharge a wash liquid into said cup after said sample has been drawn in and while said probe oscillating means is operative.

5. Apparatus according to claim 4 wherein said suction applying means comprises:
   a. a positive displacement transfer pump including a cylinder and a piston, said cylinder having an inlet-outlet port;
   b. a slide valve including a valve body having a first passage coupled to a waste outlet, a second passage coupled to said cylinder inlet-outlet port and a third passage coupled to said photometer cell, and a slideable valve member containing passage means therein for coupling said first and second passages when said valve member is in a first position and said second and third passages when said valve member is in a second position; and
   c. means for driving said piston and said valve member.

6. Apparatus according to claim 5 wherein said probe oscillating means comprise:
   a. a master piston and cylinder containing hydraulic fluid;
   b. a slave piston and cylinder flow-coupled to said master cylinder, said slave piston being mechanically coupled to said probe; and
   c. means to oscillate the piston in said master cylinder.

7. Apparatus according to claim 6 wherein said piston-oscillating means comprise a cam driving the piston of said master cylinder, said apparatus further comprising a rotary shaft mounting said cam and two additional cams respectively constituting said means for driving said transfer pump valve member all of said cams being on a common shaft.

8. Apparatus according to claim 6 further comprising:
   a. a spindle valve having a body containing first, second, third and fourth valve ports and a shiftable spindle member for controlling intercommunication among said ports, said spindle member having a first position in which of all said valve ports are isolated from one another and a second position in which the first and third ports are interconnected and the second and fourth are interconnected;
   b. conduit means connecting the first and second valve ports to a source of hydraulic fluid, the third to the lower end of the master cylinder and the fourth to the upper end of the slave cylinder;
   c. additional conduit means connecting the upper end of said master cylinder to the lower end of said slave cylinder;
   d. means resiliently urging said slave piston toward the upper end of the slave cylinder; and
   e. means for moving said spindle member between said first and second positions.

9. Apparatus according to claim 8 wherein said means to discharge wash liquid into said cup comprises:
   a. a wash pump including a cylinder and a piston, said cylinder containing an inlet-outlet port;
   b. a valve including a valve body containing first, second and third passages and a shiftable valve member controlling the intercommunication of said passages, said member having a first position in which the first and second passages are interconnected and a second position in which the second and third passages are interconnected, said first and second passages being flow-coupled respectively to a source of wash liquid and to said inlet-outlet port of the wash pump cylinder;
   c. a flow-line leading from said third passage to the cup; and
   d. means to reciprocate said piston and shift said valve member between its first and second positions.

* * * * *

UNITED STATES PATENT OFFICE
CERTIFICATE OF CORRECTION

Patent No. 3,948,607　　　　　　　　　Dated April 6, 1976

Inventor(s) John G. Atwood, et al.

It is certified that error appears in the above-identified patent and that said Letters Patent are hereby corrected as shown below:

IN THE ABSTRACT

Line 1, --a sample or batch of-- should be inserted after "transferring", and --fluid-- should be inserted after "a".

Line 2, "sample" (first occurrence) should be --mixture from a reaction cup-- and "sample" (Second occurrence) should be --photometer--.

Line 5, --transfer-- should be inserted after "coordinated" and --photometer-- should be inserted before "sample".

Line 6, "holding it there" should be --maintaining the sample stationary--.

Lines 6 and 7, "measurement" should be --photometric analysis--.

Line 8, "sample" should be --reaction--.

Column 4, line 10, "valve" should be deleted.

Column 4, line 11, --valve-- should be inserted before "bore".

Signed and Sealed this

Twenty-ninth Day of March 1977

[SEAL]

Attest:

RUTH C. MASON　　　　　　　　　　C. MARSHALL DANN
*Attesting Officer*　　　　　　　　*Commissioner of Patents and Trademarks*

UNITED STATES PATENT AND TRADEMARK OFFICE
CERTIFICATE OF CORRECTION

PATENT NO. : 3,948,607
DATED : April 6, 1976
INVENTOR(S) : John G. Atwood, et al It is certified that error appears in the above-identified patent and that said Letters Patent are hereby corrected as shown below:

Column 1, line 10, "an" should be --a copending-- and --, Serial No. 594,951 filed July 10, 1975 as a continuation of now abandoned application -- should be inserted after "al".

Column 1, lines 11 and 12, "filed on Aug. 22, 1974 and assigned to the same assignee as the present invention" should be deleted.

Column 1, line 21, "endure" should be --ensure--.

Column 1, line 42, "photometric" should be --photometer--.

Column 3, line 46, "is" should be deleted.

Claim 1, line 5, --cell-- should be inserted after "sample".

Signed and Sealed this fifth Day of July 1977

[SEAL]

Attest:

RUTH C. MASON
Attesting Officer

C. MARSHALL DANN
Commissioner of Patents and Trademarks